(12) United States Patent
Taverner et al.

(10) Patent No.: US 9,389,174 B2
(45) Date of Patent: Jul. 12, 2016

(54) TIME DIVISION MULTIPLEXING (TDM) AND WAVELENGTH DIVISION MULTIPLEXING (WDM) SENSOR ARRAYS

(71) Applicant: WEATHERFORD/LAMB, INC., Houston, TX (US)

(72) Inventors: Domino Taverner, Wallingford, CT (US); John J. Grunbeck, Northford, CT (US); Jason Scott Kiddy, Gambrills, MD (US)

(73) Assignee: WEATHERFORD TECHNOLOGY HOLDINGS, LLC, Houston, TX (US)

( * ) Notice: Subject to any disclaimer, the term of this patent is extended or adjusted under 35 U.S.C. 154(b) by 0 days.

(21) Appl. No.: 14/308,296

(22) Filed: Jun. 18, 2014

(65) Prior Publication Data

US 2015/0369731 A1 Dec. 24, 2015

(51) Int. Cl.
*G01N 21/47* (2006.01)
*G01M 11/00* (2006.01)
*G01M 11/02* (2006.01)
(Continued)

(52) U.S. Cl.
CPC ........ *G01N 21/4788* (2013.01); *E21B 47/0002* (2013.01); *G01D 5/3539* (2013.01); *G01D 5/35383* (2013.01); *G01M 11/02* (2013.01); *G01M 11/33* (2013.01);
(Continued)

(58) Field of Classification Search
CPC .......... G01N 21/4788; G01N 21/4799; G01N 2201/061; G01N 2201/0696; G01N 2201/08; E21B 47/0002; G01M 11/02; G01M 11/33; G01D 5/35383; G01D 5/3539
See application file for complete search history.

(56) References Cited

U.S. PATENT DOCUMENTS 4,713,538 A * 12/1987 Theocharous ............ 250/227.23
5,035,511 A *  7/1991 Berthold ..................... 374/124
(Continued)

FOREIGN PATENT DOCUMENTS

DE       10014175 A1   10/2001
EP        0859477 A2    8/1998
(Continued)

OTHER PUBLICATIONS

Dakin, J.P., Review Article—Multiplexed and distributed optical fibre sensor systems, J. Phys. E: Sci. Instrum. 20, p. 954, 1987.*
(Continued)

*Primary Examiner* — Peter Radkowski
(74) *Attorney, Agent, or Firm* — Patterson & Sheridan, L.L.P.

(57) ABSTRACT

Methods and apparatus for interrogating sets of optical elements having characteristic wavelengths spanning a sweep range while avoiding overlapping reflections from the different sets when performing a wavelength sweep are provided. One example method generally includes introducing a pulse of light, by an optical source, into an optical waveguide to interrogate at least first and second sets of optical elements, wherein the optical elements within each set have different characteristic wavelengths and wherein the first and second sets are separated in time such that a first time window over which light is reflected from the optical elements in the first set and reaches a receiver does not overlap with a second time window over which light is reflected from the optical elements in the second set and reaches the receiver; and processing the reflected light to determine one or more parameters corresponding to the optical elements.

21 Claims, 8 Drawing Sheets

(51) Int. Cl.
*E21B 47/00* (2012.01)
*G01D 5/353* (2006.01)

(52) U.S. Cl.
CPC . *G01N 2201/061* (2013.01); *G01N 2201/0696* (2013.01); *G01N 2201/08* (2013.01)

(56) References Cited

U.S. PATENT DOCUMENTS

| | | | |
|---|---|---|---|
| 5,189,299 A * | 2/1993 | Zimmermann et al. | 250/227.16 |
| 5,592,282 A * | 1/1997 | Hartog | 356/44 |
| 5,596,409 A * | 1/1997 | Marcus et al. | 356/479 |
| 5,680,489 A | 10/1997 | Kersey | |
| 5,757,487 A * | 5/1998 | Kersey | 356/478 |
| 6,542,228 B1 * | 4/2003 | Hartog | 356/73.1 |
| 7,274,441 B2 * | 9/2007 | Payton | 356/73.1 |
| 7,769,252 B2 * | 8/2010 | Taverner et al. | 385/12 |
| 7,859,654 B2 * | 12/2010 | Hartog | 356/73.1 |
| 7,865,044 B2 * | 1/2011 | Farhadiroushan et al. | 385/12 |
| 8,379,297 B2 * | 2/2013 | Taverner | G01J 3/1895 359/333 |
| 8,400,640 B2 * | 3/2013 | Kim | G01J 3/02 356/477 |
| 8,494,322 B2 * | 7/2013 | Kersey | E21B 47/123 385/123 |
| 2001/0017727 A1 * | 8/2001 | Sucha et al. | 359/326 |
| 2005/0068525 A1 * | 3/2005 | Taverner | H04B 10/2572 356/327 |
| 2006/0028637 A1 * | 2/2006 | Payton | 356/73.1 |
| 2007/0280703 A1 * | 12/2007 | Taverner | G01J 3/02 398/195 |
| 2008/0273852 A1 * | 11/2008 | Parker et al. | 385/128 |
| 2008/0296480 A1 * | 12/2008 | Haber | G01D 3/35303 250/227.14 |
| 2009/0174931 A1 * | 7/2009 | Huber | H01S 3/1106 359/340 |
| 2009/0202192 A1 * | 8/2009 | Taverner et al. | 385/12 |
| 2009/0290160 A1 | 11/2009 | Taverner | |
| 2010/0014071 A1 * | 1/2010 | Hartog | 356/73.1 |
| 2010/0128348 A1 | 5/2010 | Taverner | |
| 2013/0093598 A1 * | 4/2013 | Duncan et al. | 340/854.7 |
| 2014/0340235 A1 * | 11/2014 | Taverner | G01D 5/35316 340/855.3 |

FOREIGN PATENT DOCUMENTS

| | | |
|---|---|---|
| GB | 2419184 A | 4/2006 |
| WO | 2013001268 A2 | 1/2013 |
| WO | 2013043353 A1 | 3/2013 |

OTHER PUBLICATIONS

U.S. Appl. No. 14/076,766, Taverner et al.
U.S. Appl. No. 14/276,792, Taverner.
British Search Report dated Oct. 8, 2014, issued by the Intellectual Property Office of South Wales in Application No. GB1408526.0.
Huber et al., "Fourier domain mode locked lasers for OCT imaging at up to 290kHz sweep rates," Proceedings of SPIE, OSA Biomedical Optics, SPIE, US vol. 5861, Dec. 31, 2005, pp. 1-6.
International Search Report and Written Opinion dated Oct. 10, 2014 issued by the European Patent Office in Application No. PCT/US2014/038126.
International Search Report and Written Opinion dated Aug. 31, 2015, corresponding to International Application No. PCT/US2015/033914.

* cited by examiner

TIME DIVISION MULTIPLEXING (TDM) AND WAVELENGTH DIVISION MULTIPLEXING (WDM) SENSOR ARRAYS

BACKGROUND OF THE INVENTION

1. Field of the Invention

Embodiments of the present invention generally relate to interrogation of optical components and, more particularly, to techniques and apparatus for avoiding overlap of reflections from different arrays of optical elements along the same waveguide when interrogated using wavelength-swept light.

2. Description of the Related Art

Many optical components have a characteristic wavelength that may be found by interrogating the optical component with an optical source capable of producing light at various wavelengths over a fixed range or bandwidth. For example, fiber Bragg gratings (FBGs) (typically formed by photo-induced periodic modulation of the refractive index of an optical waveguide core) are highly reflective to light having wavelengths within a narrow bandwidth centered at a wavelength generally referred to as the Bragg wavelength. Because light having wavelengths outside this narrow bandwidth is passed without reflection, Bragg wavelengths can be determined by interrogating a Bragg grating with a light source swept across a bandwidth that includes the Bragg wavelength and monitoring the reflected optical power spectrum at a receiver unit. Because Bragg wavelengths are dependent on physical parameters, such as temperature and strain, Bragg gratings can be utilized in optical sensor systems to measure such parameters.

In these and a wide range of other types of optical systems, the measurement of a characteristic wavelength of an optical component to great accuracy (and/or with great repeatability) is important to system performance. Two significant parameters determining the error of any such measurement are the signal-to-noise ratio (SNR) and effective integration time of the measuring system. SNR is dependent of many factors including received optical power, optical-source noise, and receiver noise. The effective integration time is dependent on overall averaging time and the proportion of that time which is producing useful signals at the receiver unit. Improving these two parameters can improve characteristic wavelength measurement repeatability and accuracy.

Conventional swept-wavelength Bragg grating interrogators are limited in the number of sensors that can be interrogated on a single fiber by the optical bandwidth of the source because only wavelength division multiplexing (WDM) is used to interrogate the sensors. Many of the applications using Bragg grating sensors can be improved by increasing the number of sensors in the system.

In some cases, this problem has been addressed by increasing the optical bandwidth of the light source to enable more sensors to be multiplexed on the optical fiber using WDM.

In other cases, a swept-wavelength interferometry technique has been used. This technique may allow time division multiplexing (TDM) of grating sensors; however, the swept-wavelength interferometry technique may suffer from a limited spatial window range as well as limited wavelength resolution. In yet another approach, time-gated lasers have been used to TDM Bragg grating sensors.

SUMMARY OF THE INVENTION

Embodiments of the present invention generally relate to interrogating sets of optical elements having characteristic wavelengths spanning a sweep range while avoiding overlapping reflections from the different sets at a receiver when performing a wavelength sweep. Some embodiments may include delay mechanisms between the different sets of optical elements, thereby allowing the sets to be physically located in close proximity to one another.

One embodiment of the present invention is a method for optical interrogation. The method generally includes introducing a pulse of light, by an optical source, into an optical waveguide to interrogate at least first and second sets of optical elements by performing a sweep of wavelengths over a period of the pulse, wherein the optical elements within each set have different characteristic wavelengths and wherein the first and second sets are separated in time such that a first time window over which light is reflected form the optical elements in the first set and reaches a receiver does not overlap with a second time window over which light is reflected from the optical elements in the second set and reaches the receiver; and processing the reflected light to determine one or more parameters corresponding to the optical elements.

Another embodiment of the present invention is an apparatus for optical interrogation. The apparatus generally includes an optical waveguide; an optical source configured to introduce a pulse of light into the optical waveguide to interrogate at least first and second sets of optical elements by performing a sweep of wavelengths over a period of the pulse, wherein the optical elements within each set have different characteristic wavelengths; a receiver, wherein the first and second sets are separated in time such that a first time window over which light is reflected from the optical elements in the first set and reaches the receiver does not overlap with a second time window over which light is reflected from the optical elements in the second set and reaches the receiver; and a processing system configured to process the reflected light to determine one or more parameters corresponding to the optical elements.

Yet another embodiment of the present invention is a system for sensing one or more downhole parameters. The system generally includes a wellbore; an optical waveguide at least partially disposed in the wellbore; an optical source configured to introduce a pulse of light into the optical waveguide by performing a sweep of wavelengths over a period of the pulse; at least first and second sets of optical elements disposed along the optical waveguide, wherein the optical elements within each set have different characteristic wavelengths; a receiver, wherein the first and second sets are separated in time such that a first time window over which light is reflected from the optical elements in the first set and reaches the receiver does not overlap with a second time window over which light is reflected from the optical elements in the second set and reaches the receiver; and a processing system configured to process the reflected light to determine the one or more downhole parameters corresponding to the optical elements.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Embodiments of the present invention provide techniques and apparatus for interrogating arrays of time division multiplexed (TDMed) and effectively wavelength division multiplexed (WDMed) optical sensors having characteristic wavelengths spanning a sweep range while avoiding overlapping reflections from the different arrays as received at a receiver when performing a wavelength sweep. Avoiding overlap of reflections from different arrays of optical sensors may entail providing an effective time separation (e.g., a corresponding length of optical fiber) between arrays, such that reflections from one array do not overlap with reflections from another array. Some embodiments may include delay mechanisms between the different arrays of optical sensors, thereby allowing the arrays to be physically located in close proximity to one another. As used herein, the phrase "physically located in close proximity" generally refers to the distance between two arrays being shorter than a straight length of optical fiber (or other waveguide) having a round-trip delay equivalent to the effective time separation.

An Example Optical Sensor System

Figure 1A:
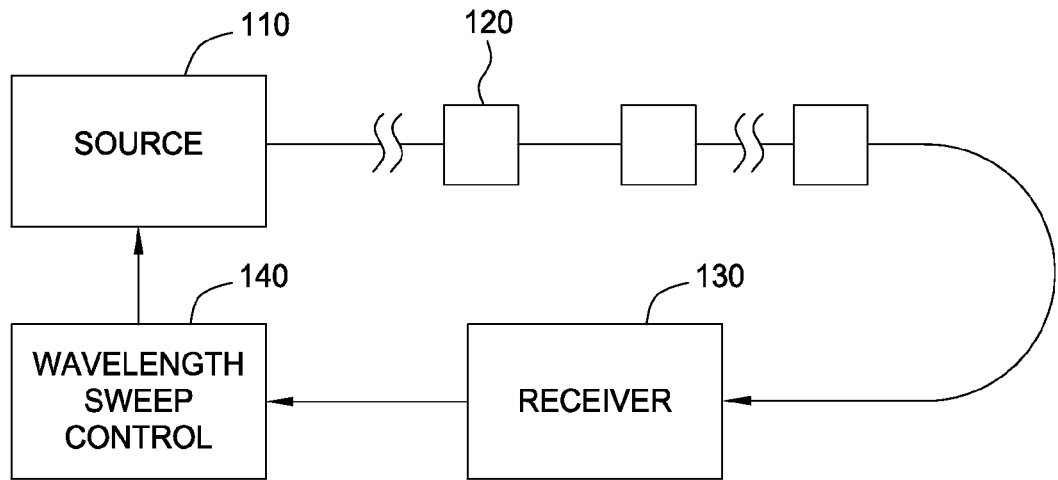
FIG. 1A illustrates an example transmissive optical sensor system with wavelength sweep control, in accordance with embodiments of the present invention.

FIG. 1A illustrates an example optical sensor system 100 utilizing wavelength sweep control in accordance with one embodiment of the present invention. As illustrated, the system 100 may include a swept-wavelength optical source 110, one or more transmissive optical elements 120 having one or more spectral features of interest (e.g., a characteristic wavelength), and a sweep control unit 140.

The swept-wavelength optical source 110 produces optical radiation at wavelengths and over wavelength ranges (bandwidths) under the control or influence of the sweep control unit 140. The elements 120 may be interrogated with optical radiation from the optical source 110 that is swept across a spectral range including the spectral features of interest. The elements 120 may be sensitive to parameters (e.g., temperatures, pressures, and strain) that affect the attenuation of particular wavelengths of light transmitted through the elements 120 in a known manner.

Figure 2:
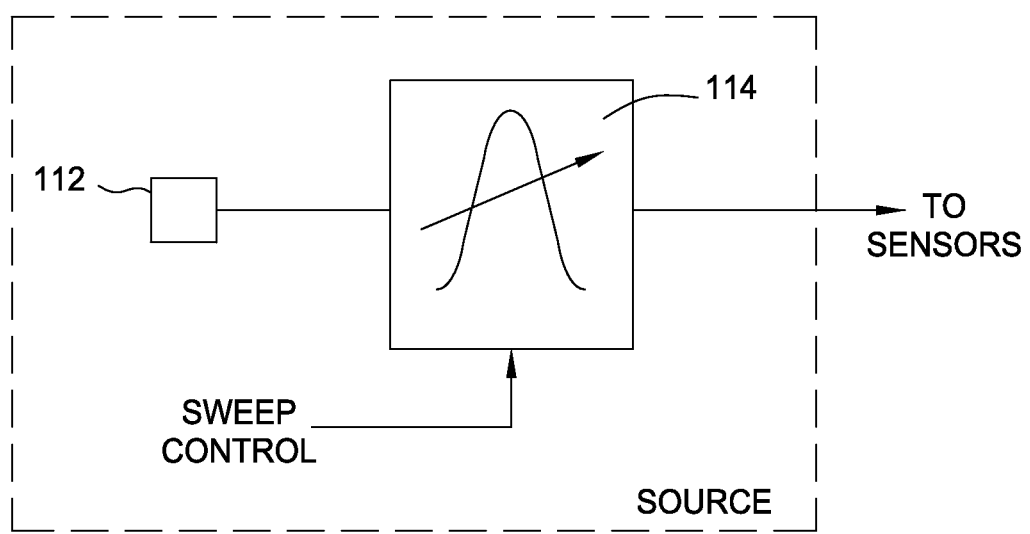
FIG. 2 illustrates an example wavelength sweeping optical source utilizing a tunable filter, in accordance with embodiments of the present invention.

As illustrated in FIG. 2, one embodiment of the optical source 110 may include a broadband source 112 and a tunable filter 114 that may be controlled by the sweep control unit 140. For example, the sweep control unit 140 may control the tunable filter 114 to adjust a wavelength range (or band) to pass with little or no attenuation while blocking wavelengths outside the range. For other embodiments, the optical source 110 may include a light source that can be controlled to generate optical signals of different wavelengths, such as a tunable laser.

Referring back to FIG. 1A, a receiver 130 may include any suitable combination of optical, opto-electronic, and electronic components to process light signals transmitted through the elements 120. Thus, the receiver 130 may be able to generate information about the corresponding parameters, based on the timing of the received light signals and any shifts therein. The receiver 130 may include any suitable combination of components that converts optical signals to electrical signals, filters, and samples. As an example, for one embodiment, the receiver may include an optical PIN diode (i.e., having a lightly doped near intrinsic semiconductor region between a p-type semiconductor region and an n-type semiconductor region), transimpedance amplifier, analog filter, analog-to-digital converter, digital filter, and processing unit (e.g., an embedded processor, industrial or personal computer) for wavelength determination.

As illustrated, the sweep control unit 140 may receive, as input, one or more signals from one or more points in the receiver 130 and, in response, may output signals that influence the sweep of the optical source 110. Examples of typical parameters that the sweep control unit may influence include, but are not limited to, source wavelength, source wavelength sweep range, sweep rate, and/or source optical output power. These influences may include discontinuous or continuous changes in such parameters, for example, multiple sweep bands. The sweep control unit signals can influence a sweep in progress and/or influence future sweeps, as described in greater detail below.

The sweep control unit 140 may be implemented using any suitable processing logic, such as an embedded controller, a programmable logic controller (PLC) or personal computer (PC). While shown as a separate component in the Figures, for some embodiments, the sweep control unit 140 may be integrated into, or be an integral function of the receiver 130, the source 110, and/or both.

Figure 1B:
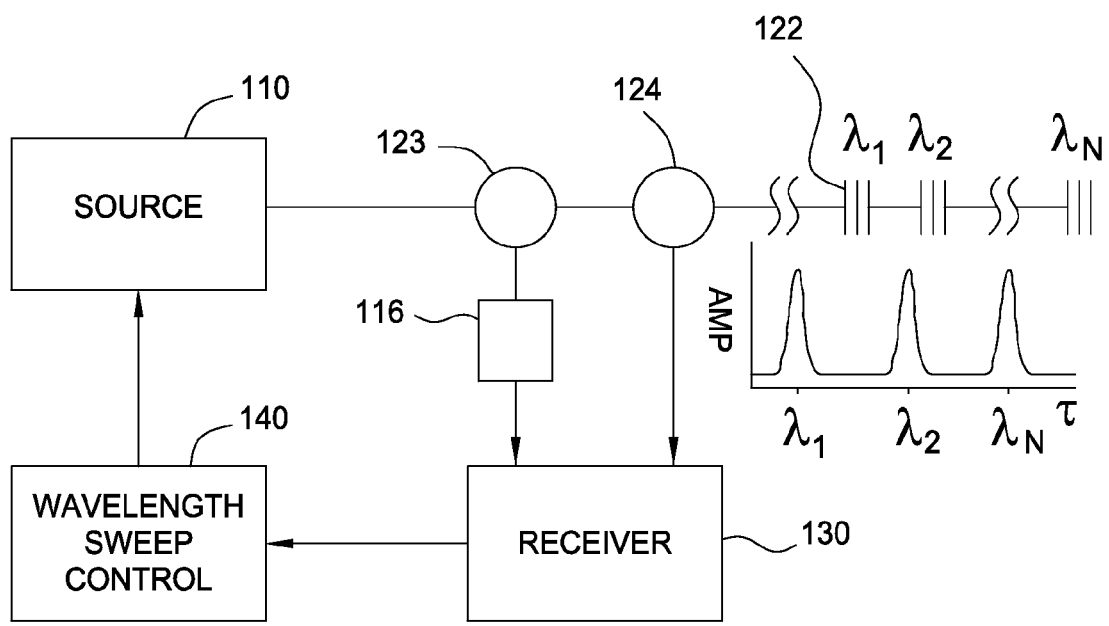
FIG. 1B illustrates an example reflective optical sensor system with wavelength sweep control, in accordance with embodiments of the present invention.

As illustrated in FIG. 1B, similar techniques may be applied to a system utilizing reflective sensor elements 122, such as Bragg gratings, with the spectral feature of the light reflected dependent upon a sensed parameter. Each Bragg grating may be interrogated by sweeping across a corresponding wavelength range chosen to contain the characteristic wavelength A, accounting for the maximum deviations in center wavelengths (areas of peak reflection) expected over the entire range of measured parameters and over time. During this interrogation, response signals are monitored by the receiver 130 in order to determine the time of the response signals, which may be used to determine the characteristic wavelength of the sensor element and, thus, the value of the sensed parameter.

Interrogating optical signals from the source 110 may be directed to the reflective sensor elements 122 via a bidirectional coupler 124 that also directs reflected response signals to the receiver 130. A splitter 123 may also direct a portion of the interrogating optical signals to a reference element 116, allowing the receiver 130 to monitor optical signals produced by the optical source 110 (e.g., the actual wavelength and power). For some embodiments, the reference element 116 may be used to measure the wavelength versus the time of the sweep. The wavelength-versus-time measurement may be used to correlate return signal times of light reflected from the sensor elements 122 with wavelengths in order to determine a value of a sensed parameter. For example, the reference element 116 may be a Fabry-Perot etalon, a gas absorption cell, etc.

Example Fast Swept Interrogation

Wavelength division multiplexing (WDM) systems are typically limited in the number of sensors that can be interrogated on a single fiber. However, using a fast-sweep tunable optical source may increase the number of sensors than can be combined on the fiber, thereby allowing distinguishing among signals from the sensors based on the timing of the received signals and the sweep and, thus, effectively providing for both WDM and time division multiplexing (TDM) on the fiber.

Figure 3:
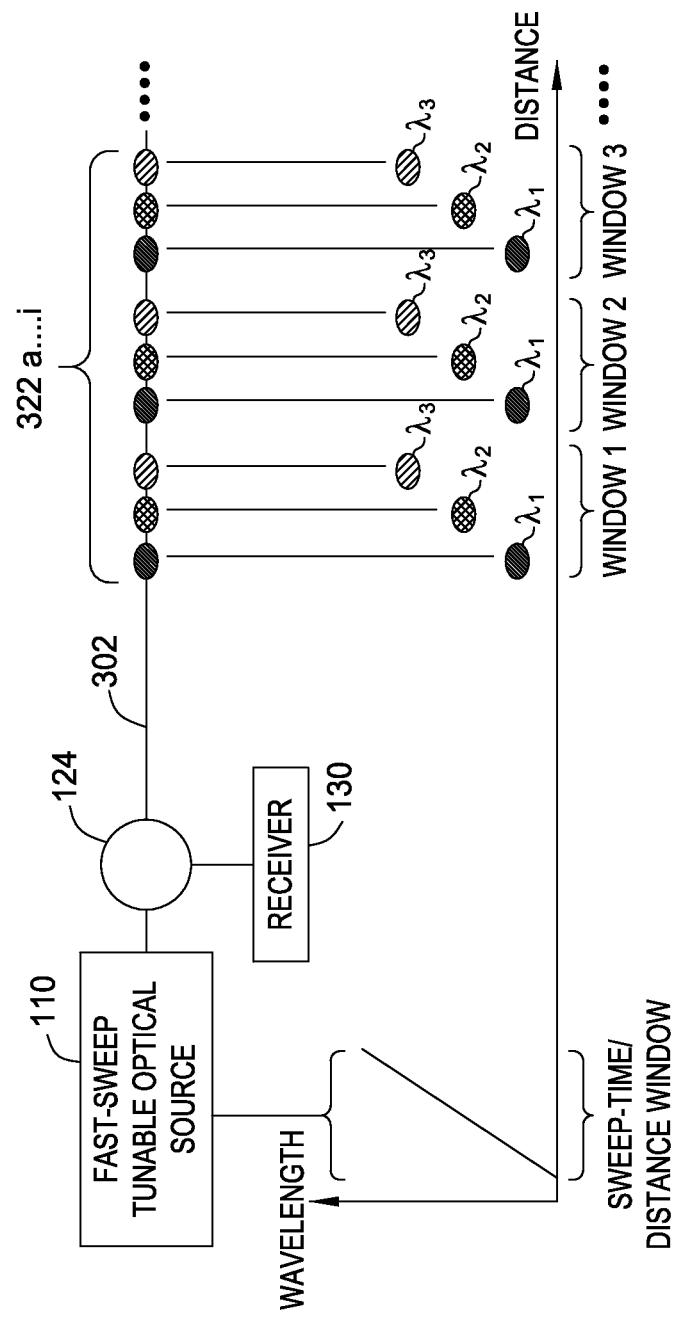
FIG. 3 illustrates example interrogation of time division multiplexed (TDMed) and effectively wavelength division multiplexed (WDMed) sensors on a single fiber using a fast-swept optical source, in accordance with embodiments of the present invention.

FIG. 3 illustrates example interrogation of TDMed and effectively WDMed sensors on a single fiber using a fast-swept tunable optical source, in accordance with embodiments of the present invention. As illustrated in FIG. 3, a tunable optical source, such as source 110 (e.g., a tunable laser or amplified spontaneous emission (ASE) source with a tunable filter) may be coupled to an optical waveguide 302 (e.g., an optical fiber) containing multiple optical elements (e.g., fiber Bragg grating (FBG) sensors) 322a . . . i to be interrogated by the optical source 110. The optical elements 322a . . . i may have characteristic wavelengths within the output wavelength capabilities of the optical source 110. An optical coupler, such as optical coupler 124, may route light reflected by the optical elements 322 to a receiver, such as receiver 130.

The receiver 130, or a separate processing unit, may be configured to process (e.g., demodulate) received signals from the optical elements 322a . . . i based on the times at which the signals are received, the sweep rate of source 110, and the relative distances of the optical elements 322a . . . i from the optical source 110 and the receiver 130 (i.e., time-of-flight). The receiver 130 may convert the optical signals to electrical signals for further processing. The tunable optical source 110 may have a fast sweep rate such that a sweep of the optical spectrum is completed in only a fraction of the time that it takes the light to travel down the optical waveguide 302 to the furthest optical element in the system, for example optical element 322i shown in FIG. 3, and be reflected back to the receiver 130 (i.e., the round-trip time). For some embodiments, this sweep is accomplished in a period less than a round-trip time to the closest optical element along the waveguide. After completing a sweep of the desired optical spectrum, the optical source 110 may be turned off or idled by outputting a wavelength which will not be reflected by any of the optical elements 322. In some embodiments, the optical source 110 may emit a chirped pulse of light.

The sweep time of the optical source 110 is used to define a sweep window within which multiple optical elements 322 can be multiplexed using WDM, so to speak. The optical elements within each set are effectively WDMed by having different characteristic wavelengths that reflect light at different times according to their individual distance along the fiber and the parameters of the wavelength sweep function (e.g., the sweep rate). The sweep time of the optical source 110, along with the wavelength direction of the sweep (e.g., short wavelengths to long wavelengths or long wavelengths to short wavelengths), the distance to and spacing of the optical elements in the WDMed set, and the ordering of the characteristic wavelengths of the optical elements in the set define a time/distance window of the light received from (e.g., reflected by) the optical elements in the set. For example, the time at which light may be received from an optical element within the set may correspond to a distance of the optical element from the optical source, as well as the characteristic wavelength of the optical element and when that wavelength occurs during the sweep (which may depend on the direction of the sweep). Therefore, a window may be defined for each set that includes the spread, in time or distance, of the light signals received from the optical elements within the set.

Therefore, in order for optical elements 322 to be multiplexed on the optical waveguide 302 using WDM, the optical elements may have different characteristic wavelengths. For example, as illustrated in FIG. 3, optical elements 322a, 322b, and 322c may be located within the sweep window and have characteristic wavelengths $\lambda\_1$, $\lambda\_2$, and $\lambda\_3$, where $\lambda\_1$, $\lambda\_2$, and $\lambda\_3$ are each different wavelengths. In this case, optical elements 322a, 322b, and 322c may be effectively WDMed on the optical waveguide 302. The receiver 130 may distinguish among signals received from the optical elements 322a, 322b, and 322c based on the time at which the signals are received, which is a function of the sweep parameters.

Additional optical elements can be multiplexed using TDM as long as they are outside the sweep windows of other sensors with the same characteristic wavelengths. For example, as illustrated in FIG. 3, optical elements 322d, 322e, and 322f may be located outside the sweep window of optical elements 322a, 322b, and 322c. Optical elements 322d, 322e, and 322f may therefore have characteristic wavelengths $\lambda\_1$, $\lambda\_2$, and $\lambda\_3$, and the optical sensors may be TDMed to distinguish therebetween. Similarly, optical elements 322g, 322h, and 322i may be outside the sweep windows of optical elements 322a, 322b, 322c, 322d, 322e, and 322f. Optical elements 322g, 322h, and 322i may therefore also have characteristic wavelengths $\lambda\_1$, $\lambda\_2$, and $\lambda\_3$, and the optical sensors may be TDMed to distinguish therebetween. In certain embodiments, optical elements 322d-322i may have characteristic wavelengths different than the first set of optical elements (e.g., $\lambda\_4$-$\lambda\_9$).

In certain embodiments, the optical elements may be in arranged in order of increasing or decreasing order of characteristic wavelength. In some embodiments, the optical elements may be arranged in any order of characteristic wavelengths (e.g., randomly). In certain embodiments, optical elements of the second set may be arranged in the same order or the reverse order of characteristic wavelengths of the optical elements in the first set. In certain embodiments, optical elements of the second set may be arranged in any order of characteristic wavelengths (e.g., randomly).

In some embodiments, the sweep rate may be about 400 kHz, corresponding to a 2.5 µs sweep time and sweep distance of 500 m in an optical fiber. In some embodiments, the sweep rate may be about 1 MHz or higher. The resolution of the sweep or sweep time may be dependent on the sample rate of the receiver 130. For example, for a 1 MHz sweep rate, a receiver may sample with a 13-bit data acquisition card.

Using the above-described approaches, multiple sets of optical elements can be multiplexed on the fiber, greatly increasing the number of sensors in the sensing system that can be distinguished. If the wavelength sweep range is reduced to cover the operational wavelength range of just one optical element, then the system may become a TDM-only system.

Example Optical Sensor Array Arrangements

As described above, a sweep window generally refers to the time (or corresponding distance) over which all of the sensor signal reflections from a single set of (effectively wavelength division multiplexed) sensors are spread when travelling back to the receiver. Thus, the optical sensors in each set may be effectively multiplexed on the fiber using WDM (based on the wavelength sweep and the different characteristic wavelengths within the set), and the sets of optical sensors may be multiplexed using TDM (based on the timing of the received signals reflected from the optical elements).

Figure 4:
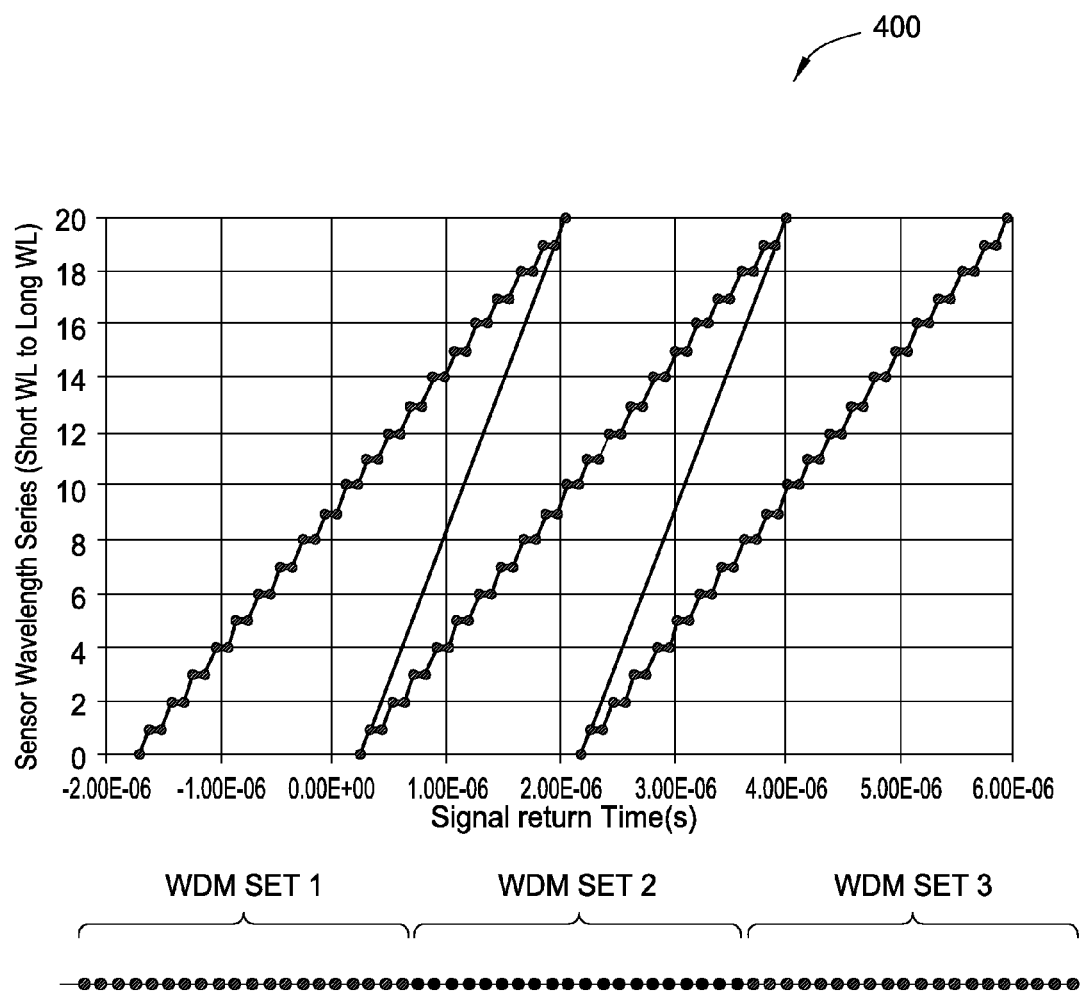
FIG. 4 illustrates example signal return times from three adjacent arrays of effectively WDMed optical sensors arranged in increasing wavelength order within each array, interrogated with a sweep of increasing wavelength from a fast-swept optical source, in accordance with embodiments of the present invention.

The ability to time domain multiplex optical sensors in an array of such sensors may be limited by the time spread of return signals from each array of effectively WDMed sensors. For example, if two adjacent sets of sensors are interrogated with a fast-swept tunable-wavelength source and positioned too closely together, return signals from the sensors may overlap. FIG. 4 is a graph 400 of example signal return times from three adjacent arrays of effectively WDMed optical sensors (labeled WDM Set 1, WDM Set 2, and WDM Set 3), where the arrays have no significant space therebetween. To generate the data in FIG. 4, each array has 20 optical sensors, each having a different characteristic wavelength spaced over 10 meters. The optical sensors within each array are arranged in increasing wavelength order (i.e., from shortest wavelength to longest wavelength) and are interrogated using a 1.9 µs linear sweep of increasing wavelength from a fast-swept tunable-wavelength source. As illustrated, return signals from adjacent arrays of sensors overlap in time. This overlap may make it difficult to determine from which array and, thus, from which sensor the return signal was reflected.

Avoiding such overlap of return signals may limit how closely the sensors can be spaced in a uniform array or force the sensors to be clustered in sets of WDM sensors with larger gaps between adjacent sets of sensors multiplexed by TDM. Either case may result in an arrangement of undesirable sensor spacings for certain sensing applications. For example, in downhole oil and gas applications—where the sensors are typically deployed in series along production tubing disposed in a wellbore, a large number of closely spaced (e.g., 1 to 20 m) sensors may be utilized to cover several kilometers of well length.

While this sensor spacing problem may be solved by using multiple optical fibers to cover the gaps between sensors, the use of multiple fibers may not be feasible for some applications, perhaps due to cost or limited fiber availability (e.g., due to a limited number of high pressure feedthroughs). Accordingly, what is needed are techniques and apparatus for avoiding overlap of reflections from different sets of optical sensors disposed along the same waveguide when interrogated using wavelength-swept light and for allowing the sets to be physically located in close proximity to one another.

Embodiments of the present invention utilize an empty length of optical fiber or other waveguide between sets of effectively WDMed sensors in an effort to avoid overlap of reflections from the different sets. As used herein, an empty length of optical fiber generally refers to a length of optical fiber without any optical sensors.

Figure 5:
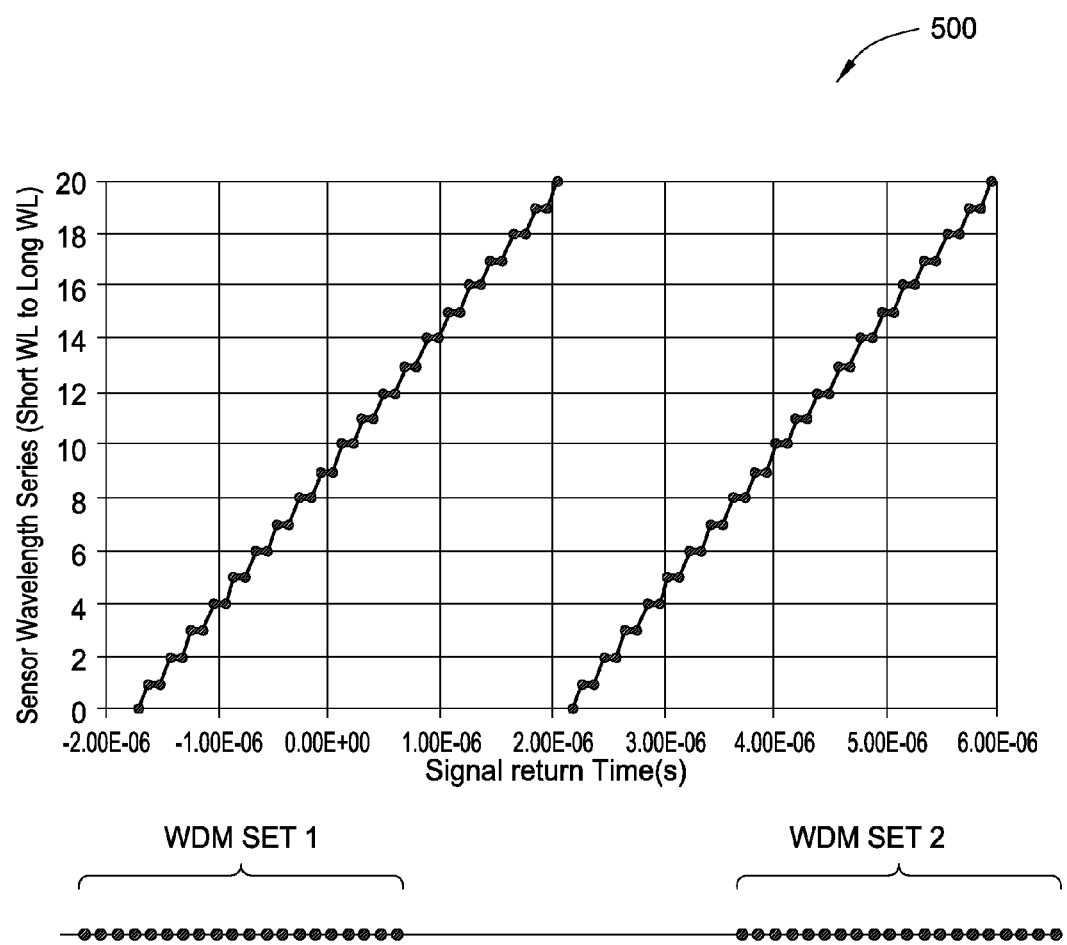
FIG. 5 illustrates example signal return times from two adjacent arrays of effectively WDMed optical sensors arranged in increasing wavelength order within each array and separated by an empty section of fiber, interrogated with a sweep of increasing wavelength from a fast-swept optical source, in accordance with embodiments of the present invention.

In contrast with FIG. 4, FIG. 5 is a graph 500 of example signal return times from two adjacent arrays of effectively WDMed optical sensors separated by an empty length of optical fiber between the two arrays (labeled WDM Set 1 and WDM Set 2). Like FIG. 4, each array has 20 optical sensors, each having a different characteristic wavelength, spaced over 10 m to generate the data in FIG. 5. However, the arrays are spaced 200 meters apart along the optical fiber. The optical sensors within each array are arranged in increasing wavelength order and are interrogated using a 1.9 µs linear sweep of increasing wavelength from a fast-swept tunable-wavelength source, As illustrated, the return signals from the first and second sets of sensors do not overlap in time.

Figure 6A:
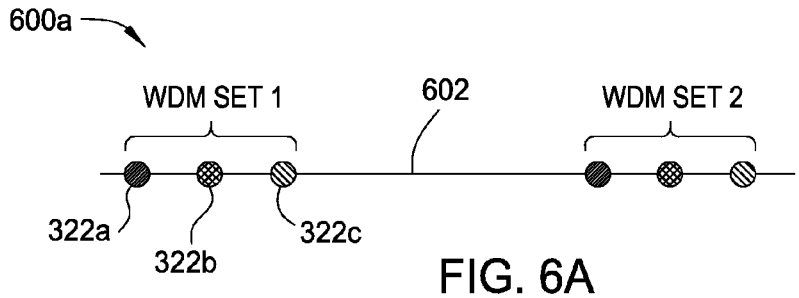
FIG. 6A illustrates an example arrangement of sets of TDMed and effectively WDMed sensors limited in closeness along the optical waveguide by the return time of the signals from the sensor sets, in accordance with embodiments of the present invention.

FIG. 6A illustrates an example arrangement 600a for solving the problem of time overlapping return signals from adjacent WDM sensor sets when interrogated with a fast-swept tunable-wavelength source, similar to the arrangement of WDM Sets 1 and 2 in FIG. 5. The arrangement 600a has a number of effectively WDMed and TDMed sensors 322 deployed along an optical fiber to perform sensing of one or more parameters (e.g., temperature or pressure). Multiple WDMed sensors 322 may be grouped into a number of sets, with each set separated by an empty length of optical fiber 602 in an effort to avoid the time overlap, given the speed of light in this optical fiber and the corresponding round-trip delay provided by this length. As illustrated in FIG. 6A the empty length of optical fiber 602 is interposed between a first set of sensors 322 (WDM Set 1) and a second set of sensors 322 (WDM Set 2) to separate reflected signals from the first and second sets of sensors in time (as depicted in the graph 500 of FIG. 5, for example), so that a receiver may determine from exactly which sensor 322 a reflected signal was returned.

Figure 6B:
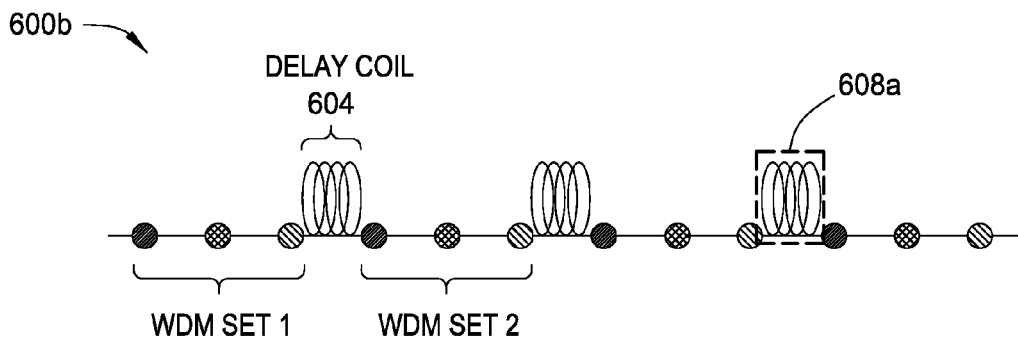
FIG. 6B illustrates an example arrangement of sets of TDMed and effectively WDMed sensors having a delay coil disposed between each sensor set, in accordance with embodiments of the present invention.
Figure 6C:
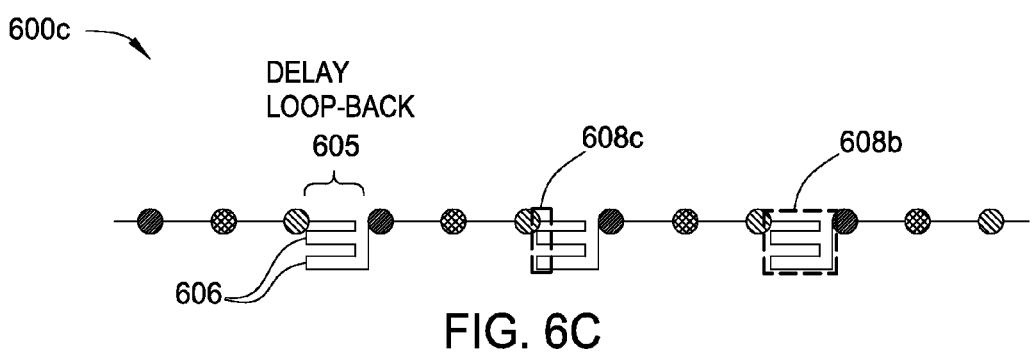
FIG. 6C illustrates an example arrangement of sets of TDMed and effectively WDMed sensors having a plurality of delay loop-backs disposed between each sensor set in accordance with embodiments of the present invention.

As illustrated in the arrangement 600a of FIG. 6A, the empty length of optical fiber 602 may be a straight length of optical fiber, without any substantial bends, turns, etc. However, such a straight section of optical fiber precludes adjacent sets of optical sensors from being physically located any closer together than the length of the empty, straight section and may also prevent the placement of sensors in a desired position. FIGS. 6B and 6C illustrate example arrangements 600b and 600c, respectively, for solving this problem by employing particular delay mechanisms between adjacent arrays of optical sensors.

FIG. 6B illustrates an example arrangement 600b of sensor arrays using a delay coil 604 as the delay mechanism, which may be positioned between any two adjacent sensor arrays as desired. The delay coil 604 may be configured such that reflected light from a first set of sensors (e.g., WDM Set 1) as received by receiver 130 does not overlap with reflected light from a second set of sensors (e.g., WDM Set 2) at the receiver. For example, delay coil 604 may comprise a length of optical fiber wound in coils with an optical distance greater than or equal to the effective time separation to avoid time overlap of reflected signals from the different sets, given the speed of light in the delay coil and the corresponding round-trip delay provided by this length of optical fiber. The delay coil 604 permits the first and second sets of sensors to be physically located closer together than a straight length of optical fiber having a round-trip delay equivalent to the effective time separation (e.g., empty, straight section of optical fiber 602 in FIG. 6A).

In an embodiment, the delay coil 604 may be mounted or otherwise disposed in a housing 608a, which may provide protection for the delay coil 604. The housing 608a may be coupled to a portion of an area in which the arrangement 600b is deployed. For example, in a downhole deployment, the housing 608a may be coupled (e.g., welded) to a sensing cable, such that the housing provides a continuous pressure barrier to the outside environment.

FIG. 6C illustrates an example arrangement 600c of optical sensor arrays using an optical fiber looped back and forth multiples times to form a delay loop-back 605 as a delay mechanism. The delay loop-back 605 may be located between any two adjacent sensor arrays as desired. The delay loop-back 605 may consist of a length of optical fiber with an optical distance greater than or equal to the effective time separation to avoid time overlap of reflected signals from the different sets, given the speed of light in the loop-back and the corresponding round-trip delay provided by this length of optical fiber. Similar to the delay coil 604, the delay loop-back 605 also permits the first and second sets of sensors to be physically located closer together than a straight length of optical fiber having a round-trip delay equivalent to the effective time separation (e.g., empty, straight section of optical fiber 602 in FIG. 6A), but avoids overlapping signal reflections therefrom as described above.

The delay loop-back 605 may be housed, at least partially, in a housing 608, which may provide protection for the loop-back. For example, the entire delay loop-back 605 may be disposed in a housing 608b, or the turns 606 for at least one end of the delay loop-back 605 may be disposed in a housing 608c. For some embodiments, the delay loop-back 605 may be implemented with a number of low-profile turns 606 to allow for a uniform diameter cable for the arrangement 600c.

Any combination of the empty lengths of optical fiber 602, the delay coils 604, and the delay loop-backs 606 may be employed between adjacent sensor arrays, along the length of the optical fiber. For example, a delay coil 604 may be used between WDM Set 1 and WDM Set 2, while an empty length of optical fiber 602 is used between WDM Set 2 and WDM Set 3. In this manner, WDM Sets 1 and 2 may be physically located in close proximity for a denser sensing area, whereas WDM Sets 2 and 3 are spaced further apart for a more sparse sensing area, for example.

Figure 7:
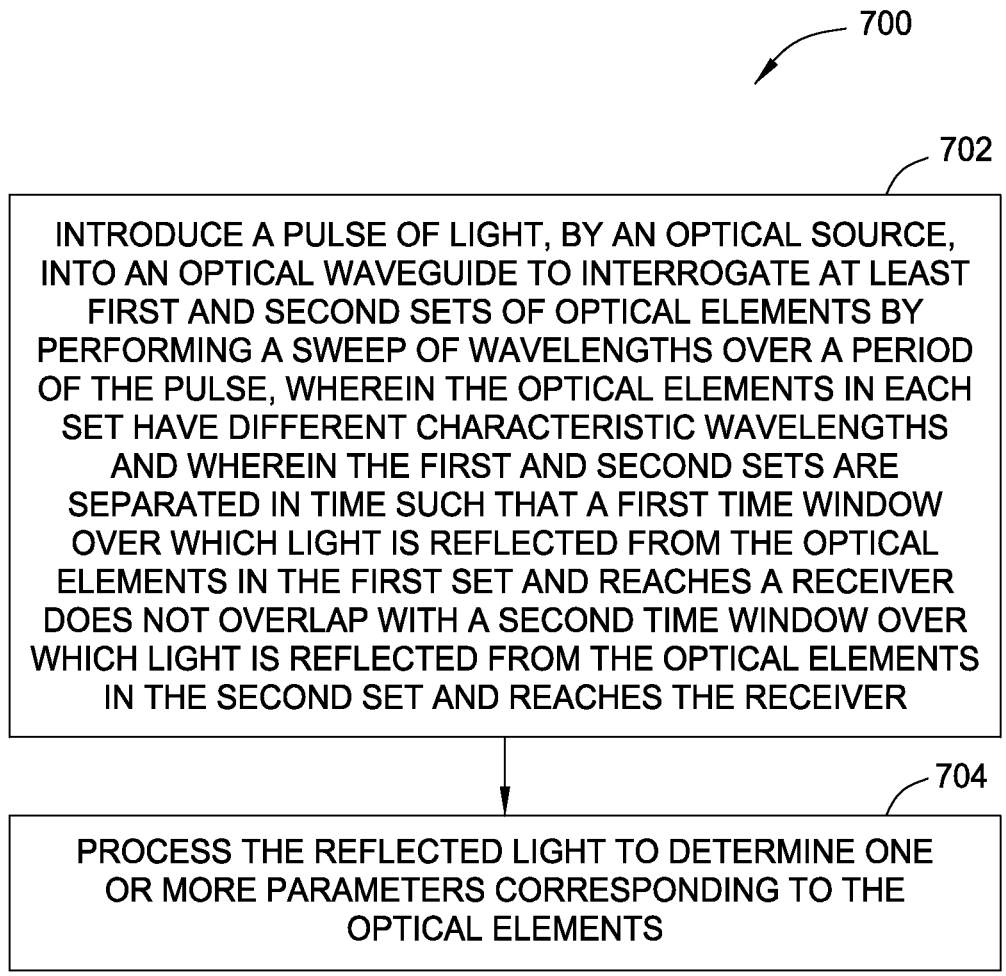
FIG. 7 is a flow diagram of example operations for interrogating multiple sets of optical elements, in accordance with embodiments of the present invention.

FIG. 7 is a flow diagram of example operations 700 for optical interrogation of sets of optical elements. Operations 700 may begin, at 702, by introducing a pulse of light into an optical waveguide to interrogate at least first and second sets of optical elements (e.g., WDM Sets 1 and 2 of optical sensors 322) by performing a sweep of wavelengths over a period of the pulse. In some embodiments, the light may be introduced by an optical source (e.g., optical source 110), which may be, for example, a tunable light source or a broadband light source (e.g., broadband source 112) together with a tunable filter (e.g., tunable filter 114). The optical waveguide may be an optical fiber, for example. The optical elements within each set have different characteristic wavelengths, and the first and second sets are effectively separated in time such that a first time window, over which light is reflected from the optical elements in the first set and reaches a receiver (e.g., receiver 130), does not overlap with a second time window, over which light is reflected from the optical elements in the second set and reaches the receiver.

For some embodiments, the optical elements may be Bragg gratings, such as fiber Bragg gratings (FBGs), which reflect light at the characteristic wavelengths. In addition or as an alternative to Bragg gratings, the optical elements may include any suitable optical sensors or other optical components having identifiable spectral features, such as Fabry-Perot structures, long period gratings (LPGs), side-hole cane waveguide sensors (e.g., as described in U.S. Pat. No. 8,494,322 to Kersey et al. and available from Weatherford/Lamb, Inc. of Houston, Tex.), and the like.

According to some embodiments, the first and second sets of optical elements are physically located closer together than a straight length of optical fiber having a round-trip delay equivalent to the effective time separation.

According to some embodiments, the first and second sets of optical elements are separated in time by a delay mechanism. For some embodiments, the delay mechanism includes a coil of optical fiber, which may be disposed in a housing (e.g., housing 608a). For other embodiments, the delay mechanism includes a loop-back of optical fiber having two or more turns. The loop-back may be disposed in a housing (e.g., housing 608b), or the turns for at least one end of the loop-back may be disposed in a housing (e.g., housing 608c).

According to some embodiments, the period of the pulse over which the sweep of wavelengths is performed, the characteristic wavelengths of the first set of optical elements, and spacing of the optical elements in the first set define the first time window. The period of the pulse over which the sweep of wavelengths is performed, the characteristic wavelengths of the second set of optical elements, and spacing of the optical elements in the second set may also define the second time window.

According to some embodiments, the optical elements in the first set have the same characteristic wavelengths as the optical elements in the second set.

At 704, the reflected light may be processed to determine one or more parameters corresponding to the optical elements. The parameters may be, for example, a sensed parameter of the downhole environment (e.g., pressure or temperature) to which the optical elements are sensitive. Processing the reflected light at 704 may involve distinguishing among response signals received from the first and second sets of optical elements based on times at which the response signals are received. In the case of FBGs, for example, the characteristic wavelengths (i.e., the wavelengths at which light is reflected back from the FBGs) may shift with a change in temperature or pressure. As such, the sensed parameter may be monitored by monitoring changes in the characteristic wavelengths of the optical elements—which may be determined by times at which signals reflected from the optical elements are detected.

Embodiments of the present invention may be applied in a number of different sensing applications, including, but not limited to, industrial applications, downhole applications (e.g., in wellbore sensing applications), and subsea applications (e.g., ocean bottom seismic sensing applications).

Figure 8:
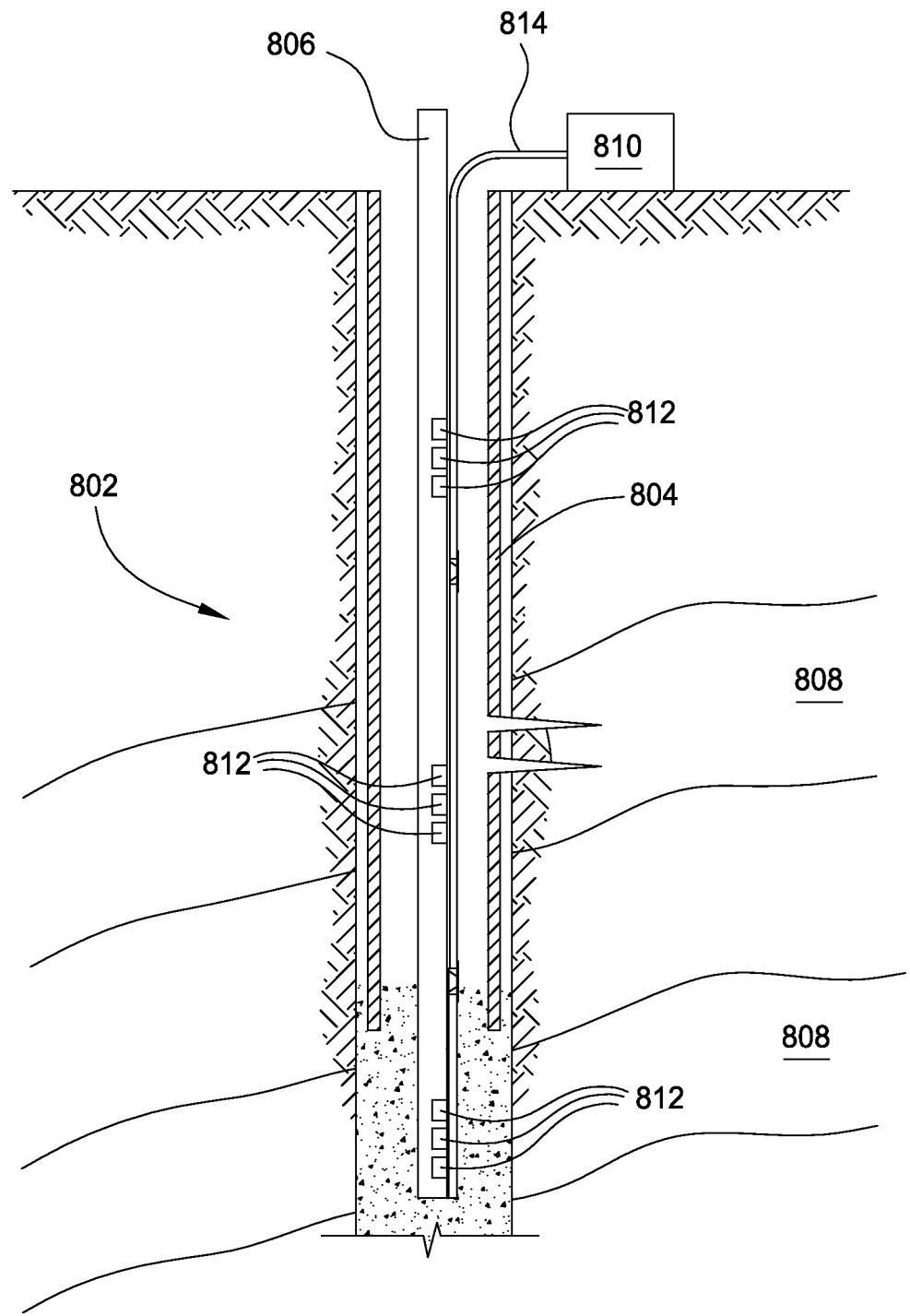
FIG. 8 is a schematic cross-sectional view of an example wellbore with multiple sensor arrays, in accordance with embodiments of the present invention.

FIG. 8 illustrates a schematic cross-sectional view of an example wellbore 802, in accordance with embodiments of the present invention. Wellbore 802 may have a casing 804 disposed within, through which production tubing 806 may be deployed as part of a wellbore completion. Hydrocarbons located in a reservoir 808 may be produced through tubing 806 using natural lift or artificial lift means. A sensing unit 810 may be used to perform sensing of a variety of parameters in a wellbore. Sensing unit 810 may be, for example, an optical system composed of an optic signal generator and a receiver for receiving data from sensor arrays 812 disposed in the wellbore.

The sensing unit 810 may be optically coupled to sensor arrays 812 (e.g., positioned in or adjacent the production tubing 806) via an optical waveguide, such as an optical fiber 814 or a cable including multiple optical fibers. Each sensor array 812 may include multiple optical sensing elements, such as FBGs or other optical components having identifiable spectral features. Each optical element within an individual sensor array 812 may have a different characteristic wavelength. A first number of sensor arrays 812 may be positioned in close proximity to each other adjacent a first production zone, a second number of sensor arrays 812 may be positioned in close proximity to each other adjacent a second production zone, and so on. For some embodiments, the sensing unit 810 may utilize a single fiber within a suspended cable deployed in production tubing 806, in a cable coupled to the outside of the production tubing 806 (i.e., in the annulus between the casing 804 and the tubing 806), or in a cable external to the casing 804.

Sensor arrays 812 may be configured such that a first time window over which light is reflected from the optical elements 322 in a first sensor array and reaches a receiver of sensing unit 810 does not overlap with a second time window over which light is reflected from the optical elements 322 in a second sensor array and reaches a receiver of sensing unit 810. Sensing unit 810 may be configured to process the reflected light to determine one or more downhole parameters corresponding to the optical elements in each sensor array 812. A delay mechanism may be interposed between the first and second sensor arrays. The delay mechanism may permit the first and second sensor arrays to be physically located in close proximity to each other, despite the optical distance (corresponding to a time separation) between the arrays.

Any of the operations described above, such as the operations 700, may be included as instructions in a computer-readable medium for execution by the receiver 130 or any other processing system. The computer-readable medium may comprise any suitable memory for storing instructions, such as read-only memory (ROM), random access memory (RAM), flash memory, an electrically erasable programmable ROM (EEPROM), a compact disc ROM (CD-ROM), or a floppy disk.

While the foregoing is directed to embodiments of the present invention, other and further embodiments of the invention may be devised without departing from the basic scope thereof, and the scope thereof is determined by the claims that follow.

The invention claimed is:

1. A method for optical interrogation, comprising:
   introducing a pulse of light, by an optical source, into an optical waveguide to interrogate at least first and second sets of optical elements by performing a sweep of wavelengths over a period of the pulse, wherein:
   the optical elements within each set have different characteristic wavelengths;
   the first and second sets are separated in time such that a first time window over which light is reflected from the optical elements in the first set and reaches a receiver does not overlap with a second time window over which light is reflected from the optical elements in the second set and reaches the receiver; and
   the first and second sets of optical elements are physically located closer together than a straight length of optical fiber having a round-trip delay equivalent to the time separation; and
   processing the reflected light to determine one or more parameters corresponding to the optical elements.

2. The method of claim 1, wherein the first and second sets of optical elements are separated in time by a delay mechanism.

3. The method of claim 2, wherein the delay mechanism comprises a coil of optical fiber.

4. The method of claim 2, wherein the delay mechanism is disposed in a housing.

5. The method of claim 2, wherein the delay mechanism comprises a loop-back of optical fiber comprising two or more turns.

6. The method of claim 5, wherein the turns for at least one end of the loop-back are disposed in a housing.

7. The method of claim 1, wherein the period of the pulse over which the sweep of wavelengths is performed, the characteristic wavelengths of the first set of optical elements, and spacing of the optical elements in the first set define the first time window.

8. The method of claim 1, wherein processing the reflected light comprises distinguishing among response signals received from the first and second sets of optical elements based on times at which the response signals are received.

9. The method of claim 1, wherein the period of the pulse over which the sweep of wavelengths is performed, the characteristic wavelengths of the second set of optical elements, and spacing of the optical elements in the second set define the second time window.

10. The method of claim 1, wherein the optical elements in the first set have the same characteristic wavelengths as the optical elements in the second set.

11. An apparatus for optical interrogation, comprising:
   an optical waveguide;
   an optical source configured to introduce a pulse of light into the optical waveguide to interrogate at least first and second sets of optical elements by performing a sweep of wavelengths over a period of the pulse, wherein the optical elements within each set have different characteristic wavelengths;
   a receiver, wherein:
     the first and second sets are separated in time such that a first time window over which light is reflected from the optical elements in the first set and reaches the receiver does not overlap with a second time window over which light is reflected from the optical elements in the second set and reaches the receiver; and
     the first and second sets of optical elements are physically located closer together than a straight length of optical fiber having a round-trip delay equivalent to the time separation; and
   a processing system configured to process the reflected light to determine one or more parameters corresponding to the optical elements.

12. The apparatus of claim 11, wherein the first and second sets of optical elements are separated in time by a delay mechanism.

13. The apparatus of claim 12, wherein the delay mechanism comprises a coil of optical fiber.

14. The apparatus of claim 12, wherein the delay mechanism is disposed in a housing.

15. The apparatus of claim 12, wherein the delay mechanism comprises a loop-back of optical fiber comprising two or more turns.

16. The apparatus of claim 15, wherein the turns for at least one end of the loop-back are disposed in a housing.

17. The apparatus of claim 11, wherein the period of the pulse over which the sweep of wavelengths is performed, the characteristic wavelengths of the first set of optical elements, and spacing of the optical elements in the first set define the first time window.

18. The apparatus of claim 11, wherein the processing system is configured to process the reflected light by distinguishing among response signals received from the first and second sets of optical elements based on times at which the response signals are received.

19. The apparatus of claim 11, wherein the period of the pulse over which the sweep of wavelengths is performed, the characteristic wavelengths of the second set of optical elements, and spacing of the optical elements in the second set define the second time window.

20. The apparatus of claim 11, wherein the optical elements in the first set have the same characteristic wavelengths as the optical elements in the second set.

21. A system for sensing one or more downhole parameters, comprising:
   a wellbore;
   an optical waveguide at least partially disposed in the wellbore;
   an optical source configured to introduce a pulse of light into the optical waveguide by performing a sweep of wavelengths over a period of the pulse;
   at least first and second sets of optical elements disposed along the optical waveguide, wherein the optical elements within each set have different characteristic wavelengths;
   a receiver, wherein:
      the first and second sets are separated in time such that a first time window over which light is reflected from the optical elements in the first set and reaches the receiver does not overlap with a second time window over which light is reflected from the optical elements in the second set and reaches the receiver; and
      the first and second sets of optical elements are physically located closer together than a straight length of optical fiber having a round-trip delay equivalent to the time separation; and
   a processing system configured to process the reflected light to determine the one or more downhole parameters corresponding to the optical elements.

* * * * *